(12) United States Patent
Bansal et al.

(10) Patent No.: US 6,368,509 B1
(45) Date of Patent: Apr. 9, 2002

(54) DEVICE FOR DIALYSIS/PURIFICATION OF PROTEINS

(75) Inventors: Parikshit Bansal, Karnal; Krishan Lal Bhatia, New Delhi, both of (IN)

(73) Assignee: National Research Development Corporation, New Delhi (IN)

( * ) Notice: Subject to any disclaimer, the term of this patent is extended or adjusted under 35 U.S.C. 154(b) by 0 days.

(21) Appl. No.: 09/122,105

(22) Filed: Jul. 24, 1998

(30) Foreign Application Priority Data

Jul. 25, 1997 (IN) ................................................ 2088/97

(51) Int. Cl.[7] ........................... B01D 61/24; B01D 61/28
(52) U.S. Cl. .................... 210/645; 210/232; 210/242.1; 210/644; 210/647
(58) Field of Search ................................ 210/232, 241, 210/242.1, 647, 644, 645

(56) References Cited

U.S. PATENT DOCUMENTS

| | | | | |
|---|---|---|---|---|
| 4,450,076 A | * | 5/1984 | Medicus et al. | 210/242.1 |
| 5,324,428 A | * | 6/1994 | Flaherty | 210/242.1 |
| 5,503,741 A | * | 4/1996 | Clark | 210/232 |
| 5,783,075 A | * | 7/1998 | Eddleman et al. | 210/242.1 |

* cited by examiner

*Primary Examiner*—John Kim
(74) *Attorney, Agent, or Firm*—Venable; George H. Spencer; Ashley J. Wells

(57) ABSTRACT

The present invention relates to a device for dialysis, desalting, purification or concentration of proteins. The device includes an upper hollow chamber, a middle detachable air-tight seal and a lower semipermeable membrane sac. The upper and lower parts are connected to each other by one or more apertures situated in the detachable air-tight seal.

18 Claims, 3 Drawing Sheets ness invented the present device for dialysis, desalting, concen-

DEVICE FOR DIALYSIS/PURIFICATION OF PROTEINS

FIELD OF THE INVENTION

The present invention relates to a device for separating substances of high molecular weight from a mixture. This invention in particular relates to a device for carrying out dialysis, purification, desalting or concentration of proteins. This invention, preferably, proposes a device which is simple to operate, manufacture and offers easy loading and recovery of protein samples.

BACKGROUND OF THE INVENTION

Dialysis is one of the most commonly utilized methods for transferring a biological sample, usually protein based, from one media to another. It is frequently necessary to remove salts or change the buffer after one step in the purification for the next step to work efficiently (e.g. in ion-exchange chromatography, the pH and/or the ionic strength may have to be changed to ensure that the protein will bind to the matrix). This is often achieved by dialysis: wherein the protein solution kept in a semi-permeable membrane is placed in the required buffer so that small molecules e.g. salts, can pass freely across the membrane whilst large molecules e.g. proteins, are retained. From the removal of salts to the exchange of buffer systems, dialysis tubing has established itself as the method of choice because it is quick and simple to use, readily available and relatively inexpensive. The semi-permeable dialysis tubing is usually made of cellulose acetate having pores of approximate size of 1–20 nm in diameter. The size of these pores determines the minimum molecular weight of molecules which will be retained by the membrane (NMWC=molecular weight cut off). Dialysis tubing often requires pre-treatment to ensure a more uniform pore size and removal of heavy metal contamination.

PRIOR ART

Traditional dialysis or desalting i.e. protein purification methods involving use of devices such as semipermeable membrane tubing are cumbersome, involving boiling, soaking, tying or clamping of membrane, which are time and effort consuming. They also result in loss of precious protein sample which loss becomes significant when sample volume is small during processing. There are various devices available for dialysis in the market manufactured by M/s.Millipore, Amicon, Pierce and Sartorium. Improved, modem methods employ tubes, having membranes fitted inside them. When these tubes, loaded with sample and are centrifuged, the smaller particles e.g. salts, low molecular weight contaminants etc. pass through, while the larger particles i.e. the proteins are retained. Thus, purification or desalting of proteins is achieved. By employing membranes of different cut-off values, proteins of different molecular weights can also be separated. The process though quick and efficient, has many limitations. For example, these tubes cannot be operated without a centrifuge, and as dialysis/purification of proteins is usually carried out at 4° C., a refrigerated centrifuge becomes essential. The utility of such methods thus becomes limited owing to essential requirement of an external, expensive piece of equipment for operation. Further, in event of interruption in the power supply, these devices cannot be utilized at all. Furthermore, the semi-permeable membranes fitted inside tubes are of a fixed volume, which restricts flexibility regarding the volume of the sample which can be processed in a single unit. Such units are quite expensive, disposable type and not capable of being reused.

U.S. Pat. No. 5,324,428 provides a disposable dialysis apparatus suspended in a dialysate solution. The dialysis apparatus has a tubular membrane which is opened at the top and bottom. A closed base membrane and collar seals the bottom of the tubular membrane. An open upper membrane and collar seals the top of the tubular membrane, and a cap may be affixed to the top of the open upper member to seal the contents. This device is rather cumbersome to operate especially when sample volumes are small e.g. less than 15 ml. Also, it is costly to manufacture and requires semipermeable membrane in tubular form which needs pretreatment e.g. boiling, before use.

U.S. Pat. No. 5,342,517 provides a filtration cassette comprising membrane filter sheets arranged in a peripherally bonded array of multilayered character wherein the filter sheets alternate with foraminous (e.g., screen or mesh) sheet elements and a cross-flow filter comprising a multiplicity of stacked filtration cassettes of such type. The device is a complicated one, suited as an on-line device for dialysis of a flowing solution or a single solution. The multiplicity of such units required when a large number of protein samples have to be processed make it unsuitable for routine laboratory use.

U.S. Pat. No. 5,503,741 provides a device for dialysis with hermetically sealed vacant chamber. The said device consists of a semi-permeable membrane sealed in a plastic frame. Sample is loaded and recovered with help of a syringe. The device though an improvement over traditional methods of dialysis, has several limitations. Firstly, the semi-permeable membrane is fixed in a frame, which restricts flexibility regarding volume of sample to be processed i.e. cassettes are of fixed size. For larger volumes, multiple cassettes have to be used for same sample or larger sized cassettes are needed. Secondly, sample loading as well as recovery, involves use of syringe and needle which causes sample loss due to sticking The sample losses can be significant when handling small volumes since the sample sticks to the walls of the gasket and syringe. In case of multiple samples, a number of syringes equal to number of samples, are required which makes the loading and recovery of sample, time consuming, tedious and expensive besides posing the risk of accidentally puncturing the membrane or causing injury to user. Thirdly, the cassettes are not reusable, and the entire unit has to be discarded after single use. Fourthly, removal of membrane protecting agent viz. glycerol, from the membrane is quite cumbersome requiring injection of distilled water into the cassette and running it in distilled water for a minimum of four hours. Lastly, the cassettes are quite expensive and cannot be reused, which is a limitation requiring special manufacturing facilities owing to nature of their design.

SUMMARY OF THE PRESENT INVENTION

As such in order to overcome the drawbacks of the hitherto known devices for dialysis, the applicants have invented the present device for dialysis, desalting, concentration or purification of proteins. The said device comprises of three parts viz. upper hollow chamber, middle detachable air-tight seal and lower semipermeable sac, the upper and lower parts being connected to each other by one or more apertures located in the detachable air-tight seal.

The main object of the present invention is to provide a simple and cost-effective device for dialysis, desalting, concentration or purification of proteins.

Another object of the invention is to provide a device for dialysis of proteins which is easy to manufacture and easy to operate.

Yet another objective of the invention is to provide a device for dialysis which offers considerable flexibility regarding volume of the sample to be processed.

Still another object of the invention is to provide a device that can be reused for the same sample or for different samples.

Another object of the present invention is to provide a device for dialysis wherein sample loading and unloading is extremely easy without any loss of sample.

One more object of the present invention is to provide a device for dialysis wherein no external equipment such as centrifuge or syringe is used and the process sample remains untouched by hand.

To meet the above and other objects, the present invention provides a device for dialysis/desalting/purification/concentration of proteins, consisting of three parts viz. upper hollow float chamber, middle detachable, air-tight seal and lower semipermeable sac, the upper and lower parts being connected to each other by an aperture in the detachable air-tight seal.

The hollow float chamber can be made of any suitable shape but preferably cylindrical and made of any suitable material such as rigid or flexible plastic, glass or rubber. The hollow chamber can be made of transparent material sample to see the sample and the chamber can be graded/graduated for easy volume measurement.

The detachable air-tight seal attached to the hollow chamber, is preferably circular, made of any suitable material such as rigid or flexible plastic and rubber and has one or more apertures which may or may not be centrally located The sac of semipermeable membrane is detachably attached to the air-tight seal.

The protein sample to be purified is put into the semi-permeable sac via the aperture in the seal, and seal is then attached to hollow chamber in any conventional manner, after which the device is floated in a tank of buffer/distilled water, for subjecting the sample to dialysis/purification/desalting.

In a preferred embodiment, the device is placed in a concentrating solution e.g. Polyethylene glycol (PEG), instead of water or buffer such as ammonium bicarbonate and water is drawn out through the semi-permeable membrane, resulting in the protein sample getting concentrated.

The purified/concentrated sample is then recovered by removing the device from the tank and inverting to device so that the sample drains from sac into the hollow float chamber, which is then opened by detaching air-tight seal, for recovering sample.

The invention is described with reference to the accompanying drawings and it should not be construed to limit the scope of the invention.

BRIEF DESCRIPTION OF THE DRAWINGS

In the accompanying drawings:

FIG. 1(*b*): Shows of the hollow float chamber having an open end and a beak for easy pouring of the contents.

FIG. 2(*a*): Illustrates formation of semi-permeable membrane sac.

FIG. 2(*b*): Shows loading of sample in the semi-permeable membrane sac.

FIG. 2(*c*): Shows sealing of semi-permeable membrane sac loaded with sample.

FIG. 2(*d*): Shows attachment of float-sheet.

FIG. 3(*a*): Shows the method of using the fully assembled device to separate high molecular weight molecules from a mixture of molecules .

FIGS. 3(*b*) & (*c*): Shows recovery of purified protein.

FIG. 3(*d*): Shows removal of air-tight seal from the hollow cylinder.

DETAILED DESCRIPTION OF THE PREFERRED EMBODIMENT

Figure 1A:
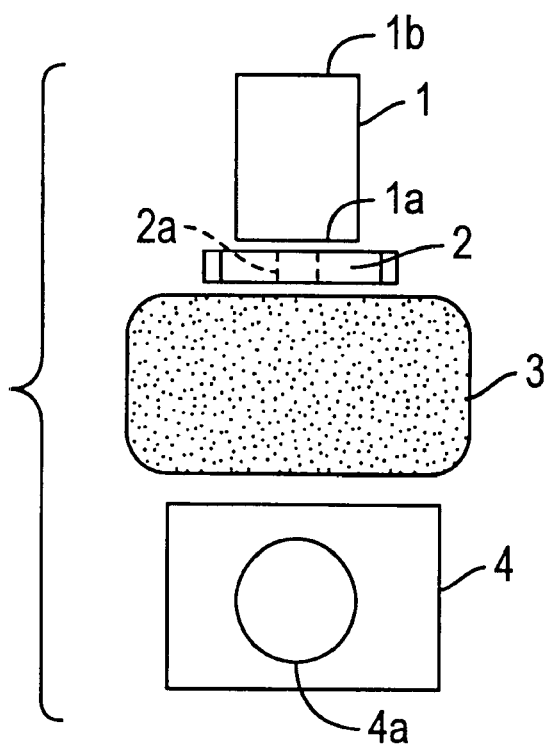
FIG. 1(*a*): Illustrates the various components of the device.
Figure 1B:
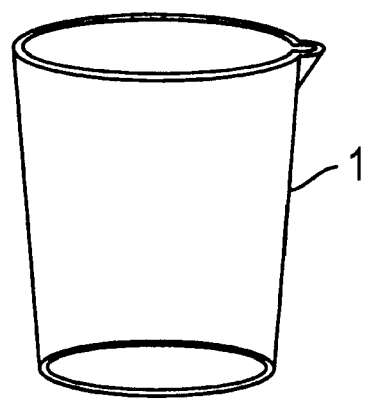

The device has the following components as indicated in FIG. 1(*a*):

A hollow float chamber (1) open at one end 1*a* and closed at the other end 1*b*, said chamber 1 preferably being cylindrical in shape and made of any suitable material such as rigid or flexible plastic material, e.g. polypropylene and preferably transparent and chemically inert. The hollow chamber top 1*b* is flat and ensures that chamber can be conveniently placed on any flat surface for sample recovery, without any need for external support, rack etc.

A preferably circular, detachable, air-tight seal (2) with one or more apertures 2*a*, preferably one central aperture and made of any suitable flexible material e.g. plastic or rubber to ensure tight-fit. The seal 2 fits tightly over the open end 1*a* of the float chamber 1, closing it effectively. The aperture 2*a* provides passage for a semipermeable membrane sac 3, sample loading as well as collection and also helps connect hollow-float-chamber 1 with semi-permeable sac 3.

A semi-permeable membrane (3) which is in the form of cut-sheets of any geometrical shape. For convenience, circular cut-sheets are preferred. Membrane 3 with different cut-off values can be used, depending upon molecular weighs of proteins to be separated or purified.

An optional means namely a float sheet (4) with central aperture corresponding to diameter of float-chamber for keeping the device floating vertically. A larger sheet with several apertures can be used for running multiple units simultaneously. The float sheet however is not an essential part of the device, for if the hollow-float-chamber 1 is of a shape that it will not topple over on being floated, and the use of float sheet can be avoided.

The device is assembled as illustrated in FIGS. 2(*a*)–2(*d*), as follows:

FIG. 2(*a*) Semi-permeable membrane sac formation— The sheet of semipermeable membrane 3 is placed over the apertures 2*a*, preferably a single central aperture of the air-tight seal 2, on side which faces the float chamber 1 on sealing, and with help of any suitable means 5 such as a glass rod, flat plastic object (if the aperture is in the form of a slit) or even a sterile gloved finger, gently pushed through the aperture 2*a*. A sac is formed on removing the glass rod/flat plastic piece. The depth of the sac formed can be easily adjusted depending upon the volume of sample to be processed. In case of larger volumes, more of the membrane 3 can be pushed through the aperture 2a, forming a deeper and/or a larger sac.

Figure 2A:
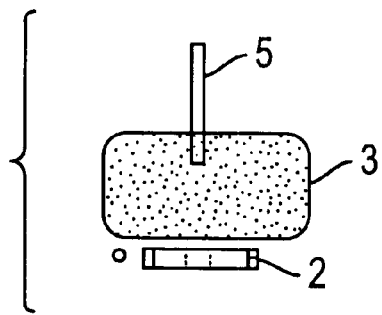
FIGS. 2(*a*): to (*d*): Illustrate the process of assembling the device.
Figure 2B:
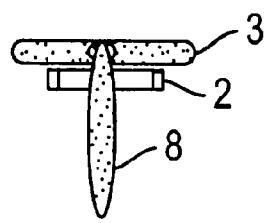

FIG. 2(b) Sample loading—The sample 8 to be processed, is simply poured directly into the sac formed, via the opening at top of the sac. This is quite easy as opening is wide enough. Alternatively, sample 8 can also be poured into float chamber, as on inversion, sample 8 will automatically drain and fill the semi-permeable membrane sac.

Figure 2C:
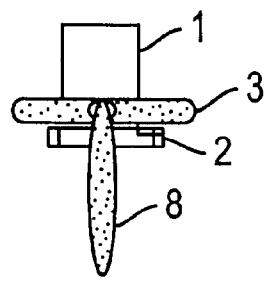

FIG. 2(c) Sealing of semi-permeable membrane sac, loaded with sample—This is done by pushing the air-tight seal 2 against edges of hollow float-chamber 1, so that it fits tightly and forms an air-tight seal. The sac of semi-permeable membrane 3, loaded with sample 8 is now sealed.

Figure 2D:
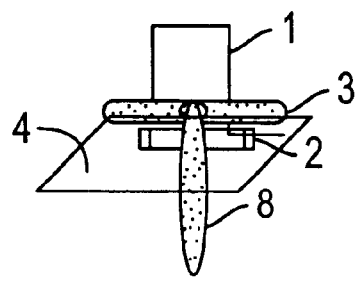

FIG. 2(d) Attachment of float-sheet—The float-sheet 4 with central aperture 4a is passed over the closed end of float chamber, till it comes to rest against rim of seal.

Device is now fully assembled and ready for use.

Figure 3A:
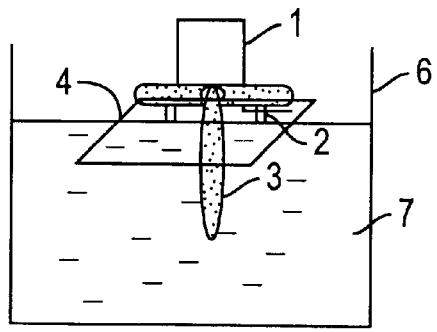
FIGS. 3(*a* to (*d*): Illustrate operation of the device and the sample recovery process.

Referring to operation of device, it is carried out as follows:

FIG. 3(a) The fully assembled device is floated in a beaker/chamber 6 filled with distilled water or any buffer 7 such as phosphate and ammonium bicarbonate, as per methodology requirement. The compact size of the device enables it to be floated in a small container such as a beaker, which can be conveniently placed in a refrigerator, if the requirement is for cold conditions during the dialysis/protein purification process.

Figures 3B, 3C:
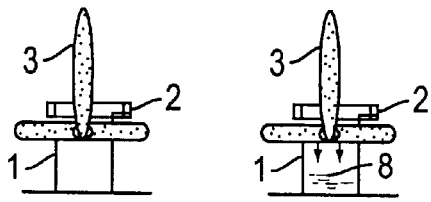

FIG. 3(b) After end of dialysis/protein purification process, the sample 8 is ready for recovery. The device is removed from the beaker/chamber 6 containing buffer 7 and simply inverted i.e. the float chamber 1 is lower to dialysis sac, and placed on a flat surface. The flat end 1b of the float chamber 1 enables it to be conveniently placed on bench top or in a refrigerator.

FIG. 3(c) Within a few minutes, the processed sample 8 under the influence of gravity drains from the semi-permeable membrane sac 3, down into the hollow-float chamber 1.

Figure 3D:
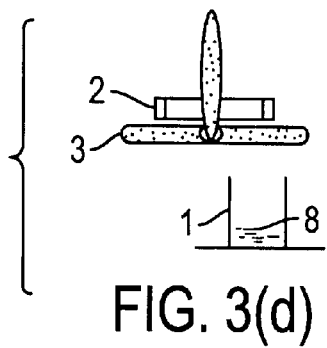

FIG. 3(d) The air-tight seal 2 is removed and the sample 8 can now be poured out or processed further (e.g. lyophilized) in the container itself and thus, remains untouched by hand.

Since the process does not involve any tying, clamping, use of syringe and needle etc. for loading or recovery of sample, the device makes dialysis/protein purification simple, quick, safe and efficient. The ease of assembly and operation of the device flexibility in terms of sample volume processing and rapid, simple method of recovering the processed sample makes it extremely useful for laboratory procedures involving dialysis/desalting/purification/concentration of proteins.

During the dialysis process, dilution of sample proteins is a common problem arising due to uptake of water or buffer. When this occurs, it is desirable to return the sample to its original concentration or to concentrate it even further. This can be easily carried out in the present device, by placing it in a solution such as that of polyethylene glycol or powder of a polymer such as sephadex, that draws water through the semi-permeable membrane. Solutions of polyethylene glycol (PEG) (mol. wt $\geq$ 20,000) at a concentration of 20% w/v are commonly used. Thus, apart from dialysis/desalting/purification of proteins, the same device can also be used for concentration of processed proteins/protein samples This offers benefits as follows.

Firstly, sample loss is minimized as dialysis and concentration are carried out in same device. Hence, losses due to transfer to a second device for concentration, are altogether avoided.

Secondly, ease of use: Concentration of protein samples is made remarkably simple, as the device has simply to be placed in a concentrating solution and removed when desired decrease in volume i.e. concentration has occurred, which can be assessed quickly if float chamber is graduated.

The preparation of membrane sac, the assembly, the utilization, the dismantling, the sterilization and the cleaning of the whole of the device according to the invention are simple. The apparatus has overall small dimensions and is readily transportable.

Figure 4:
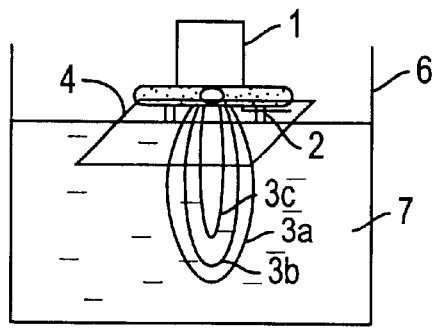
FIG. 4 shows a multilayered semipermeable sac construction of the device.

In another embodiment as shown in FIG. 4, the invention provides multisac construction for separation of proteins of different molecular weights, using membranes of different pore sizes. For example to separate proteins of molecular weights less than 25,000 and 50,000 or more from a mixture of proteins molecules, firstly a larger semi-permeable membrane sac 3a which could retain proteins of smaller molecular weight of 25,000 and less is formed by a method described above and distilled water or a buffer is poured into the sac to give it a proper shape. Thereafter, a smaller semi-permeable membrane sac 3b, 3c having larger pore size capable of retaining proteins of molecular weight 50,000 and above is owned and placed inside the larger sac, which is then attached to the hollow-float chamber by air tight seal. The multilayered sacs 3b, 3c can even be performed in different sizes which are then attached to the air tight seal in any known manner.

Naturally, embodiments of the principle of the invention other than those described by way of example may be carried out, without departing from the scope of this invention. For example, hollow chamber may be a shape other than cylindrical, and may have conical top than flat, for convenient collection of small sample volumes. The conical top can be encased in a collar, to enable the device to stand on a flat surface on inversion. Advantageously, the hollow chamber may have open top or a top which can be opened.

Moreover, material of construction of device can be varied and need not be plastic alone. Glass or any other suitable material can be used. Similarly, air-tight seal 2 may have a shape other than circular and aperture in the seal may not necessarily be central or of any particular shape. The thickness of seal 2 may also be varied depending upon convenience of use and constructing material, which can be any suitable material apart from plastic. The seal can be of "push-type" without any threads, or internally screw-threaded for engagement with externally threaded open mouth of hollow chamber, thus acting like "screw-type" lid or have small clamps for securing it to the hollow-float chamber, the basic function remaining unchanged i.e. to connect hollow chamber with membrane sac. Membranes formed by supports of various materials and covered with coatings of various nature may be employed for semi-permeable membrane sac formation. Alternatively, prefabricated sacs/tubes, available separately or attached to seal, can be used. The semi-permeable membrane sheets may be of natural or synthetic material and may or may not be provided with additional support e.g. of textile or other material. The sac may be elongated sufficiently to form a long tube, to carry greater volume of sample, may take various forms and be movable or stationary, the basic function being to act as a semi-permeable barrier between sample and the surrounding medium i.e. buffer or distilled water. For special requirements involving processing of sample under sterile conditions, autoclavable material or any other material which can suitably be sterilized, may be used in construction of device.

The present invention is considerably more effective than previously known devices used for the same purpose and does not suffer from the disadvantages of hitherto known devices. In fact, the present device offers several advantages as detailed below:

i. Low-cost, simple device, which does not require any sealing of membrane with thread, clamp etc. making the assembly process quick and easy.

ii. Offers considerable flexibility regarding volume of sample to be processed. The same device can be used to process a wide range of sample volumes.

iii. Does not require any external equipment e.g. centrifuge for its operation.

iv. Sample loading is extremely easy, as sample can simply be poured into the semi-permeable membrane sac, as per design of the device.

v. The sample recovery process is quick, efficient and simple, involving only inversion of device. Processed sample remains untouched by hand.

vi. Safe and easy sample loading and recovery, as no syringe, needle or any other external device is required.

vii. Since membrane is not fixed in any frame, but is provided separately, its washing to remove any protecting agent is fast, easy and simple.

viii. The unit is cost-effective as it can be used any number of times and need not be discarded after single-use. Only the membrane requires replacement.

ix. Low-cost, mass production of the device can easily be carried out. Owing to its simple design, no special manufacturing facilities are required to be setup.

x. Scale-up is easy owing to simple design.

xi. Separation of different sized molecules from a mixture of molecules can be performed in a single operation using multilayered semi-permeable sacs in the same device.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

We claim:

1. A device for dialysis/desalting/purification/concentration of proteins, comprising:
   an upper hollow float chamber;
   a middle detachable air-tight seal having at least one aperture therein; and
   a lower semipermeable membrane sac,
   wherein an interior of the hollow float chamber and an interior of the semipermeable membrane sac are connected to each other by the at least one aperture in the detachable air-tight seal, and wherein multiple semipermeable membrane sacs of different pore sizes are located one inside of another to separate molecules of different molecular sizes.

2. A method of at least one of dialysis, desalting, and purification of protein, comprising the steps of:
   providing the reusable device according to claim 1;
   placing a protein sample to be purified into the interior of one of the multiple semi-permeable membrane sacs via the at least one aperture in the detachable air-tight seal;
   attaching the detachable air-tight seal to the hollow float chamber; and
   floating the reusable device in a tank containing buffered distilled water for subjecting the protein sample to at least one of dialysis, desalting, and purification.

3. A method of concentrating proteins, comprising the steps of:
   providing the reusable device according to claim 1;
   placing a protein sample to be concentrated into one of multiple semi-permeable sacs via the at least one aperture in the detachable air-tight seal;
   attaching the detachable air-tight seal to the hollow float chamber; and
   floating the reusable device in a concentrating solution so that water is drawn out of the protein sample through the multiple semi-permeable membrane sacs and the protein sample is concentrated.

4. A reusable device for at least one of dialysis, desalting, purification, and concentration of proteins, comprising:
   at least one membrane sac which is semi-permeable;
   means for air-tight sealing which is detachable and which has a central hole defined there through for receiving the at least one membrane sac; and
   a hollow float chamber which is multi-functional, which is made of a floatable material, which is positioned above the at least one membrane sac, which has a flat closed end and an open end positioned opposite to the flat closed end including an opening in flow communication with the at least one membrane sac, and which is detachably sealed to the at least one membrane sac by the means for air-tight sealing.

5. The reusable device according to claim 4 wherein the hollow float chamber has a cylindrical shape.

6. The reusable device according to claim 4, wherein the hollow float chamber has a cylindrical shape and has a beak to facilitate pouring.

7. The reusable device according to claim 4, wherein the closed end of the hollow float chamber has any shape including a flat top and is comprised of at least one material selected from the group consisting of rigid plastic, flexible plastic, glass, and rubber.

8. The reusable device according to claim 4, wherein the hollow float chamber has a cylindrical shape.

9. The reusable device according to claim 8, wherein the means for air-tight sealing has a circular shape and is comprised of at least one material selected from the group consisting of rigid plastic, flexible plastic, and rubber.

10. The reusable device according to claim 4, wherein the means for air-tight sealing has a circular shape and is comprised of at least one material selected from the group consisting of rigid plastic, flexible plastic, and rubber.

11. The reusable device according to claim 4, wherein the at least one membrane sac has a plurality of membranes which are semi-permeable, and wherein each membrane of the plurality of membranes has a different pore size to separate molecules of different molecular sizes respectively during use of the reusable device.

12. The reusable device as claimed in claim 11, wherein the plurality of membranes are located one inside of another to separate molecules having different molecular sizes.

13. The reusable device as claimed in claim 12, wherein the hollow float chamber is cylindrical.

14. The reusable device as claimed in claim 4, further comprising a float sheet which has a central aperture defined there through with a shape corresponding to that of the exterior of the hollow chamber, and which is positioned around the exterior of the hollow chamber to provide at least one of floatation and floatation stability.

15. A method of at least one of dialysis, desalting, and purification of protein, comprising the steps of:
providing the reusable device according to claim 4;
placing a protein sample to be purified into one of the at least one membrane sac via the central hole in the means for air-tight sealing;
attaching the means for air-tight sealing to the hollow float chamber; and
floating the reusable device in a tank containing buffered distilled water for subjecting the protein sample to at least one of dialysis, desalting, and purification.

16. The method according to claim 15, further comprising the steps of:
removing the reusable device from the tank;
inverting the reusable device so that the protein sample drains from the at least one membrane sac into the hollow float chamber; and
detaching the hollow float chamber from detachable means for air-tight sealing for recovering the protein sample.

17. A method of concentrating proteins, comprising the steps of:
providing a reusable device according to claim 4;
placing a protein sample to be concentrated into one of the at least one membrane sac via the central hole in the means for air-tight sealing;
attaching the means for air-tight sealing to the hollow float chamber; and
floating the reusable device in a concentrating solution so that water is drawn out of the protein sample through the at least one membrane sac and the protein sample is concentrated.

18. The method according to claim 17, further comprising the steps of:
removing the reusable device from the tank;
inverting the reusable device so that the protein sample drains from the at least one membrane sac into the hollow float chamber; and
detaching the hollow float chamber from the means for air-tight sealing for recovering the protein sample.

* * * * *